US010166400B2

(12) United States Patent
Lee et al.

(10) Patent No.: US 10,166,400 B2
(45) Date of Patent: Jan. 1, 2019

(54) METHOD FOR SEPARATING NANOGENERATOR AND METHOD FOR MANUFACTURING NANOGENERATOR USING THE SAME

(71) Applicant: KOREA ADVANCED INSTITUTE OF SCIENCE AND TECHNOLOGY, Daejeon (KR)

(72) Inventors: Keon Jae Lee, Daejeon (KR); Myung Hwan Byun, Daejeon (KR); Kwi Il Park, Gyeongsangbuk-do (KR); Geon Tae Hwang, Daejeon (KR); Chang Kyu Chung, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 712 days.

(21) Appl. No.: 14/538,154

(22) Filed: Nov. 11, 2014

(65) Prior Publication Data
US 2015/0224324 A1 Aug. 13, 2015

(30) Foreign Application Priority Data

Feb. 12, 2014 (KR) ........................ 10-2014-0015885

(51) Int. Cl.
*A61N 1/00* (2006.01)
*B32B 38/00* (2006.01)
(Continued)

(52) U.S. Cl.
CPC ......... *A61N 1/3785* (2013.01); *A61N 1/3605* (2013.01); *B32B 38/10* (2013.01);
(Continued)

(58) Field of Classification Search
CPC .. A61N 1/3785; A61N 1/3605; A61N 1/0551; A61N 1/36125; A61N 1/3756; B32B 38/00; B32B 2457/00; H01L 41/113; H01L 41/312; B82Y 40/00; Y10S 322/00; Y10S 977/948
See application file for complete search history.

(56) References Cited

U.S. PATENT DOCUMENTS

2013/0334930 A1* 12/2013 Kang .................... H01L 41/113
310/339

* cited by examiner

Primary Examiner — Linda L Gray
(74) Attorney, Agent, or Firm — Rabin & Berdo, P.C.

(57) ABSTRACT

Provided is a method for separating a nanogenerator, which includes laminating a buffer layer on a sacrificial substrate, making a nanogenerator on the buffer layer, laminating a metal layer on the nanogenerator and separating the nanogenerator from the buffer layer.
Here, a nanogenerator is separated by using a stress difference between the sacrificial substrate and the metal layer, instead of an existing method in which a nanogenerator is separated from the sacrificial substrate by means of wet etching or the like. In particular, according to a difference between a tensile stress at the metal layer such as nickel and a compressive stress at the lower silicon substrate, the nanogenerator is intactly separated from the silicon oxide layer serving as a buffer layer. Therefore, the nanogenerator may be separated from the sacrificial substrate in a mechanical way, which is safer and more economic in comparison to an existing chemical separation method using an etching solution. Further, it is also possible to avoid a damage of the nanogenerator caused by an etching solution.

11 Claims, 15 Drawing Sheets

(51) Int. Cl.
  *H01L 41/08*     (2006.01)
  *A61N 1/378*     (2006.01)
  *B32B 38/10*     (2006.01)
  *A61N 1/36*      (2006.01)
  *H01L 41/113*    (2006.01)
  *H01L 41/312*    (2013.01)
  *B82Y 40/00*     (2011.01)
  *A61N 1/375*     (2006.01)
  *A61N 1/05*      (2006.01)

(52) U.S. Cl.
  CPC .......... *H01L 41/113* (2013.01); *H01L 41/312* (2013.01); *A61N 1/0551* (2013.01); *A61N 1/36125* (2013.01); *A61N 1/3756* (2013.01); *B32B 2457/00* (2013.01); *B82Y 40/00* (2013.01); *Y10S 322/00* (2013.01); *Y10S 977/948* (2013.01)

METHOD FOR SEPARATING NANOGENERATOR AND METHOD FOR MANUFACTURING NANOGENERATOR USING THE SAME

CROSS-REFERENCE TO RELATED APPLICATIONS

This application claims priority under 35 U.S.C. § 119 to Korean Patent Application No. 2014-0015885, filed on Feb. 12, 2014, in the Korean Intellectual Property Office, the disclosure of which is incorporated herein by reference in its entirety.

TECHNICAL FIELD

The following disclosure relates to a method for separating a nanogenerator using a buffer layer and a method for manufacturing a flexible nanogenerator, and in particular, to a method for separating a nanogenerator using a buffer layer and a method for manufacturing a flexible nanogenerator, in which a nanogenerator is intactly separated from a boundary surface without a separate etching process by using a stress difference between a sacrificial substrate and a metal layer so that a solid thin film nanogenerator may be separated from the sacrificial substrate in a mechanical way, thereby ensuring a safe and economic process in comparison to an existing chemical separation method using an etching solution.

BACKGROUND

Along with the development of information communication, a new-type high-performance flexible element is recently needed. In order to operate such an electronic element, a flexible energy element technique for supplying and storing an energy source is required together with a high-performance semiconductor element. However, until now, it has been impossible to implement a high-performance energy producing or storing technique due to a limit of a flexible substance which does not endure a high-temperature process. A general power producing element such as a piezoelectric element is manufactured from a hard silicon substrate and then intactly used because such an element is manufactured through a high-temperature semiconductor process. However, due to such a limit of an element substrate, applications of piezoelectric elements, secondary batteries or the like are limited.

In particular, a piezoelectric element is one of elements whose effect is limited due to such a limitation. The piezoelectric element means an element which exhibits a piezoelectricity phenomenon. The piezoelectric element is also called a piezoelectric effect element, and crystal, tourmaline, Rochelle salt or the like have been used as piezoelectric elements from old times. Artificial crystals such as lead zirconium oxide, barium titanate (BaTiO3, hereinafter, also referred to as BTO), ammonium dihydrogen phosphate, tartaric acid ethylene diamine or the like, recently developed, also have excellent piezoelectricity, and more excellent piezoelectricity may be induced by doping.

At the present, the piezoelectric element is used for generating electricity according to a pressure applied from the outside. However, if the piezoelectric element is applied to a flexible substrate which may freely bend, the piezoelectric element may instantly convert the bending of the flexible substrate into electric energy. From now, however, a piezoelectric element, particularly a large-scale piezoelectric element, applied to a flexible substrate is not yet proposed.

Further, in order to charge the generated electric energy, a charging unit is generally provided separately out of a BTO element. However, this occupies an excessive area of a device which uses the piezoelectric element.

In addition, a nanogenerator manufactured through a high-temperature process should be separated from a sacrificial substrate, which is a very important process, but at the present, a general element is separated by means of an etching process using a chemical solution. However, in this case, the device may be damaged by the etching solution, workers may be exposed to dangerous working environments, and the device may be deformed by the etching solution.

SUMMARY

An embodiment of the present disclosure is directed to providing a new method for separating a nanogenerator and a method for manufacturing a flexible nanogenerator using the same.

In an aspect of the present disclosure, there is provided a method for separating a nanogenerator, which includes: laminating a buffer layer on a sacrificial substrate; making a nanogenerator on the buffer layer; laminating a metal layer on the nanogenerator; and separating the nanogenerator from the buffer layer.

According to an embodiment of the present disclosure, the buffer layer may be a silicon oxide, and the separating of the nanogenerator from the buffer layer may be performed by applying a mechanical or thermal energy to the metal layer.

According to an embodiment of the present disclosure, by applying a mechanical or thermal energy to the metal layer, a residual tensile stress may be generated at the metal layer, and the difference between the residual tensile stress generated at the metal layer and the residual compressive stress at the sacrificial substrate may be stronger than an adhesive force between the buffer layer and the nanogenerator.

According to an embodiment of the present disclosure, the sacrificial substrate may be a silicon substrate, and the metal layer may be a nickel layer.

In another aspect of the present disclosure, there is provided a method for manufacturing a flexible nanogenerator, which includes: separating a nanogenerator according to the above method; and transferring the separated nanogenerator to a flexible substrate.

In another aspect of the present disclosure, there is provided a flexible nanogenerator, which is manufactured by the above method.

In the present disclosure, a nanogenerator is separated by using a stress difference between a sacrificial substrate and a metal layer, instead of an existing manner of separating a nanogenerator from a sacrificial substrate by means of wet etching or the like. In particular, a nanogenerator is intactly separated from a silicon oxide layer serving as a buffer layer according to a difference between a tensile stress of the metal layer such as nickel and a compressive stress of a silicon substrate at a lower portion. Therefore, the nanogenerator may be separated from the sacrificial substrate in a mechanical way, which is safer and more economic in comparison to a chemical separating method using an etching solution. Further, it is also possible to prevent the nanogenerator from being damaged by an etching solution.

DETAILED DESCRIPTION OF EMBODIMENTS

Figure 1:
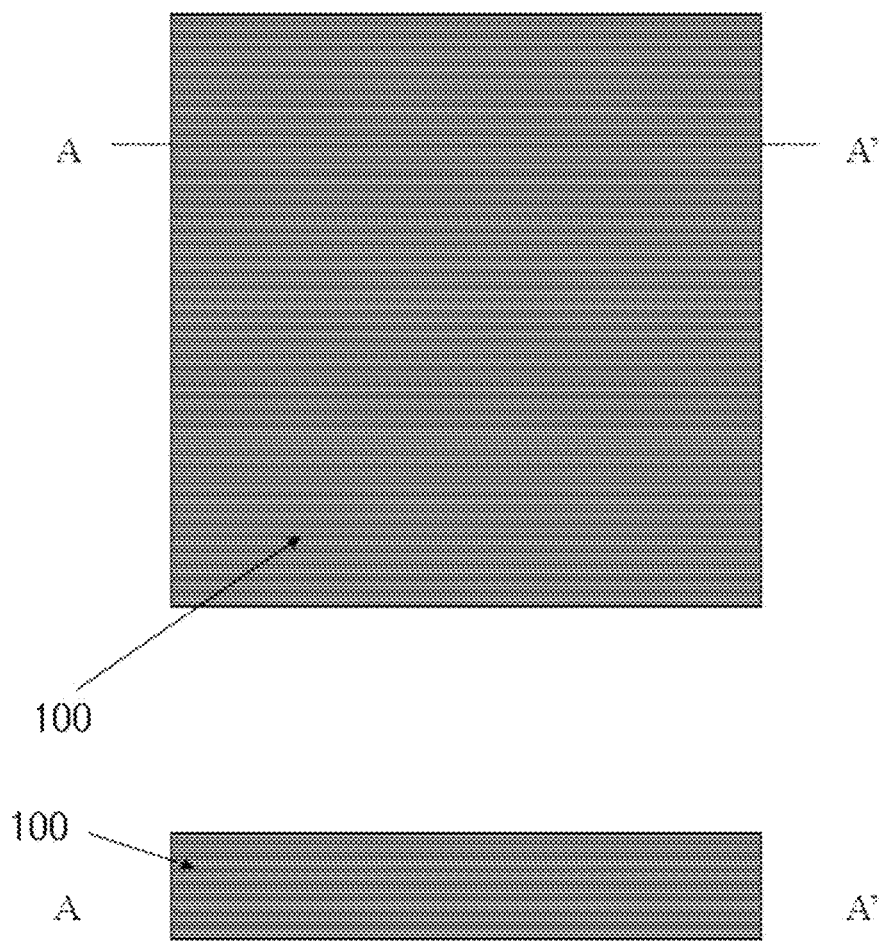
FIGS. 1 to 11 are plane views and cross-sectional views for illustrating each step of a method for manufacturing a nanogenerator according to an embodiment of the present disclosure.

Hereinafter, a method for manufacturing a nanogenerator according to each embodiment of the present disclosure will be described with reference to the accompanying drawings.

The following embodiments are just examples for helping a person skilled in the art to fully understand the present disclosure. Therefore, equivalents having the same functions as the present disclosure will also be included in the scope of the present disclosure.

In addition, regarding reference symbols endowed to components in each drawing, the same component is designated by the same reference symbol, if possible, even though it is depicted in various drawings. Moreover, in the description, details of well-known features and techniques may be omitted to avoid unnecessarily obscuring the presented embodiments.

In addition, in the present disclosure, terms or symbols such as "first", "second", "A", "B", "(a)", "(b)" or the like may be used. However, such terms or symbols are just to distinguish any component from other components and do not imply any particular nature, order or sequence of components. If it is written that any component is "connected", "coupled" or "joined" to another component, it should be understood that still another component may also be "connected", "coupled" or "joined" between these components, without being limited to the case in which these components are directly connected or joined to each other.

A nanogenerator based on a piezoelectric material is prepared on a sacrificial substrate of the present disclosure, and a silicon oxide layer serving as a buffer layer is prepared on a silicon substrate. After that, a metal layer is laminated on the device, and a mechanical or thermal energy is applied to the metal layer so that the nanogenerator is intactly separated from the silicon oxide layer serving as a buffer layer. In this specification, the nanogenerator means a fine power generating element capable of self-producing an electric current by an external physical force such as bending of a substrate.

The present disclosure has a distinctive feature in that a device (or, a nanogenerator) is effectively separated from a sacrificial substrate having a buffer layer by using a stress difference between the metal layer and the sacrificial substrate and by providing a separate buffer layer between the nanogenerator and the sacrificial substrate. In other words, the device is intactly separated from the sacrificial substrate by applying an adhesive force corresponding to the stress difference to the buffer layer (or, the silicon oxide layer). If a buffer layer having such a weak adhesive force is not used, the sacrificial substrate may be partially torn out due to a mechanical transferring method using a stress difference.

In an embodiment of the present disclosure, a device such as a nanogenerator is manufactured using an existing technique, and this is not described in detail here.

In the present disclosure, the stress difference is a difference between a tensile stress of a metal layer strongly adhered to an upper portion of the device and a compressive stress of a sacrificial substrate connected to a lower portion of the device by means of the buffer layer, and a crack occurs if a stretching force of the metal layer due to an external energy and a compressing force of the sacrificial substrate due to the stretching of the metal layer are not endured. In particular, the inventor has designed so that a portion where such a crack may occur is made of a buffer layer, which is adhered to the device with a weaker strength, instead of a sacrificial substrate. In an embodiment of the present disclosure, the buffer layer is a silicon oxide.

According to the present disclosure, since a crack occurs intactly at a boundary surface between the buffer layer and the device, an etching process is not separately required after transferring, and the device may be separated from the sacrificial substrate just in a mechanical manner, which is safer and more economic in comparison to a chemical separation method using an etching solution. Hereinafter, the present disclosure will be described in more detail based on an embodiment using a nanogenerator as the device.

FIGS. 1 to 11 are plane views and cross-sectional views for illustrating each step of a method for manufacturing a nanogenerator according to an embodiment of the present disclosure.

Referring to FIG. 1, a silicon substrate 100 serving as a sacrificial substrate is depicted. In the present disclosure, the sacrificial substrate 100 gives a stress deviator with respect to a metal layer which is laminated later, but the sacrificial substrate 100 does not come into direct contact with a nanogenerator (or, a device). In an embodiment of the present disclosure, the compressive stress of the silicon substrate 100 is not harmonious with a tensile stress of a metal layer adhered to an upper portion of the device, and a separate buffer layer (a silicon oxide layer in an embodiment of the present disclosure) adhered onto the silicon substrate 100 is cracked due to an external energy applied later. This horizontal crack of the buffer layer will be described in more detail later. In the present disclosure, particularly, the cracked portion may be adjusted and controlled according to a stress difference between the metal layer and the sacrificial substrate.

Figure 2:
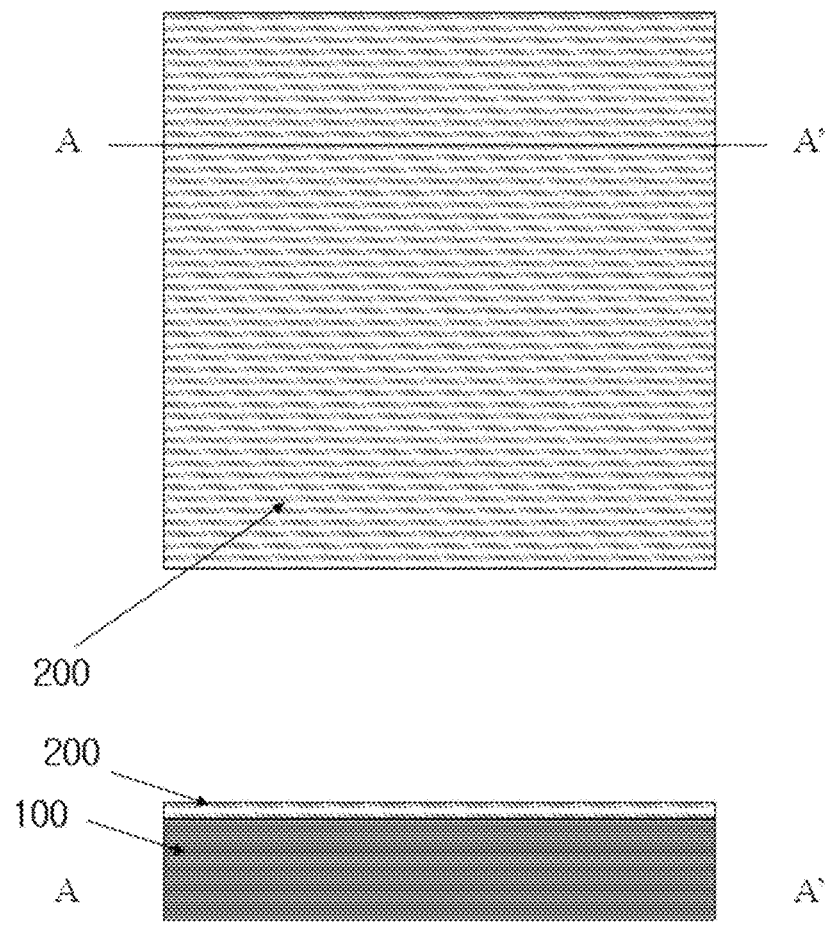

Referring to FIG. 2, a buffer layer 200 such as a silicon oxide is laminated on the silicon substrate 100. In the present disclosure, the buffer layer 200 is adhered to the nanogenerator in a level where the buffer layer 200 may be separated by a physical force generated by the stress difference. In an embodiment of the present disclosure, a silicon oxide layer is employed as the buffer layer 200, and an adhesive force between the silicon oxide layer and the nanogenerator ensures the nanogenerator to be effectively separated by a stress difference between the lower substrate and the metal layer.

Figure 3:
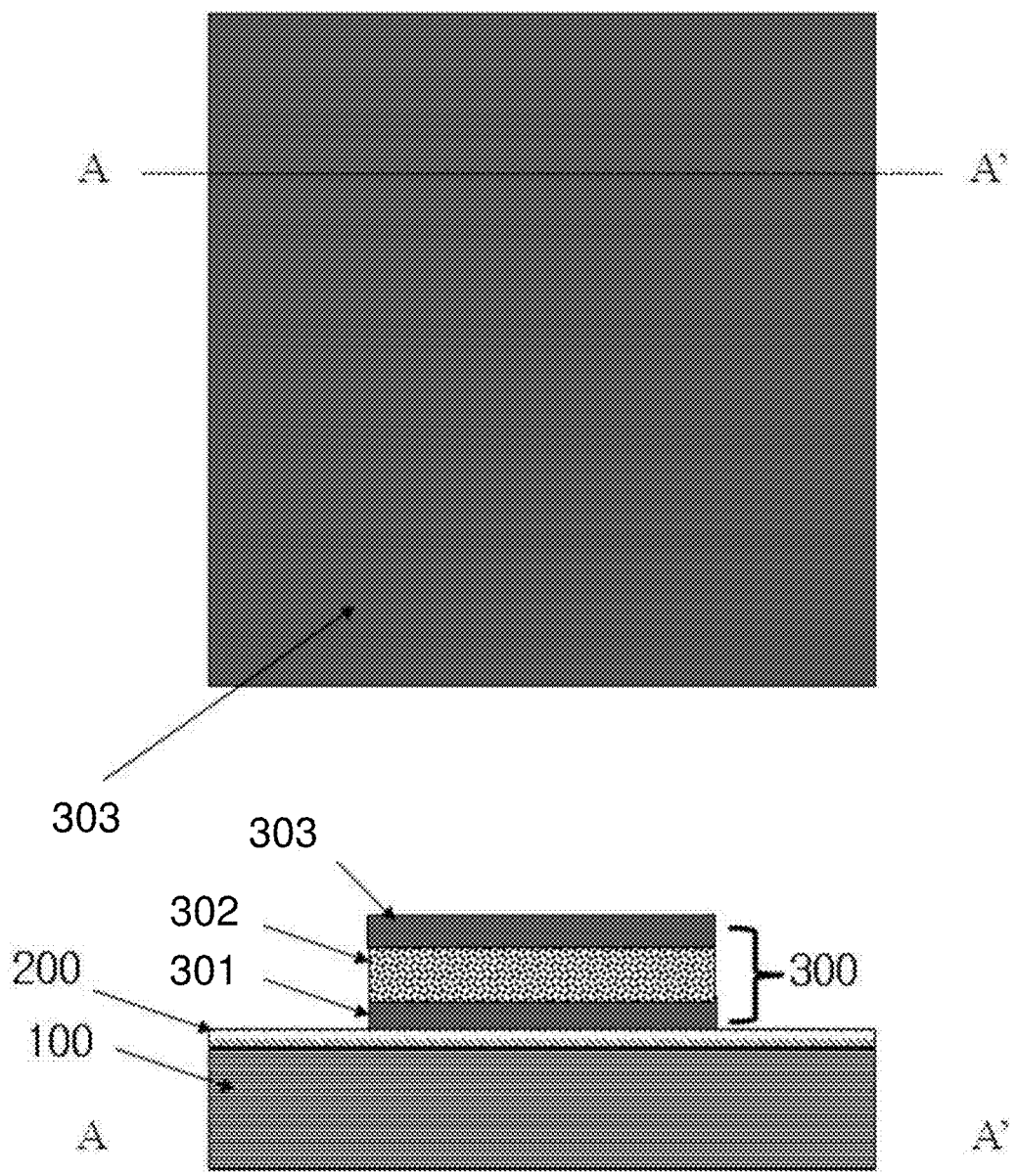

Referring to FIG. 3, a lower electrode layer 301, a piezoelectric material layer 302 and an upper electrode layer 303 are laminated in order on the buffer layer 200 which is the silicon oxide, thereby making a nanogenerator 300 with a MIM (metal-Insulator-metal) structure. The piezoelectric material layer 302 is a power generation layer which produces an electric current by bending of a flexible substrate which is transferred later. In the embodiment of the present disclosure, the piezoelectric material layer 302 is BTO, but the present disclosure is not limited thereto.

The lower electrode layer, the piezoelectric material layer and the upper electrode layer may be laminated using a conventional metal lamination process, and after lamination, a thermal treatment process may be performed to manufacture a nanogenerator with a piezoelectric material such as BTO. Through this thermal treatment process, the piezoelectric material is crystalized, and then a voltage different is applied again between the upper electrode and the lower electrode to form an electric field. If the applied electric field is greater, a leakage current is also increased further, which prevents an electric field from being normally formed. To solve this problem, the leakage current may be minimized by increasing a thickness of the BTO or forming an isolation material (not shown) on or below the piezoelectric material layer such as BTO. In particular, in the present disclosure, a high-temperature thermal treatment process and a voltage applying process are performed at the sacrificial substrate such as silicon, and thus a process limit caused by the use of a flexible substrate may be eliminated.

Figure 4:
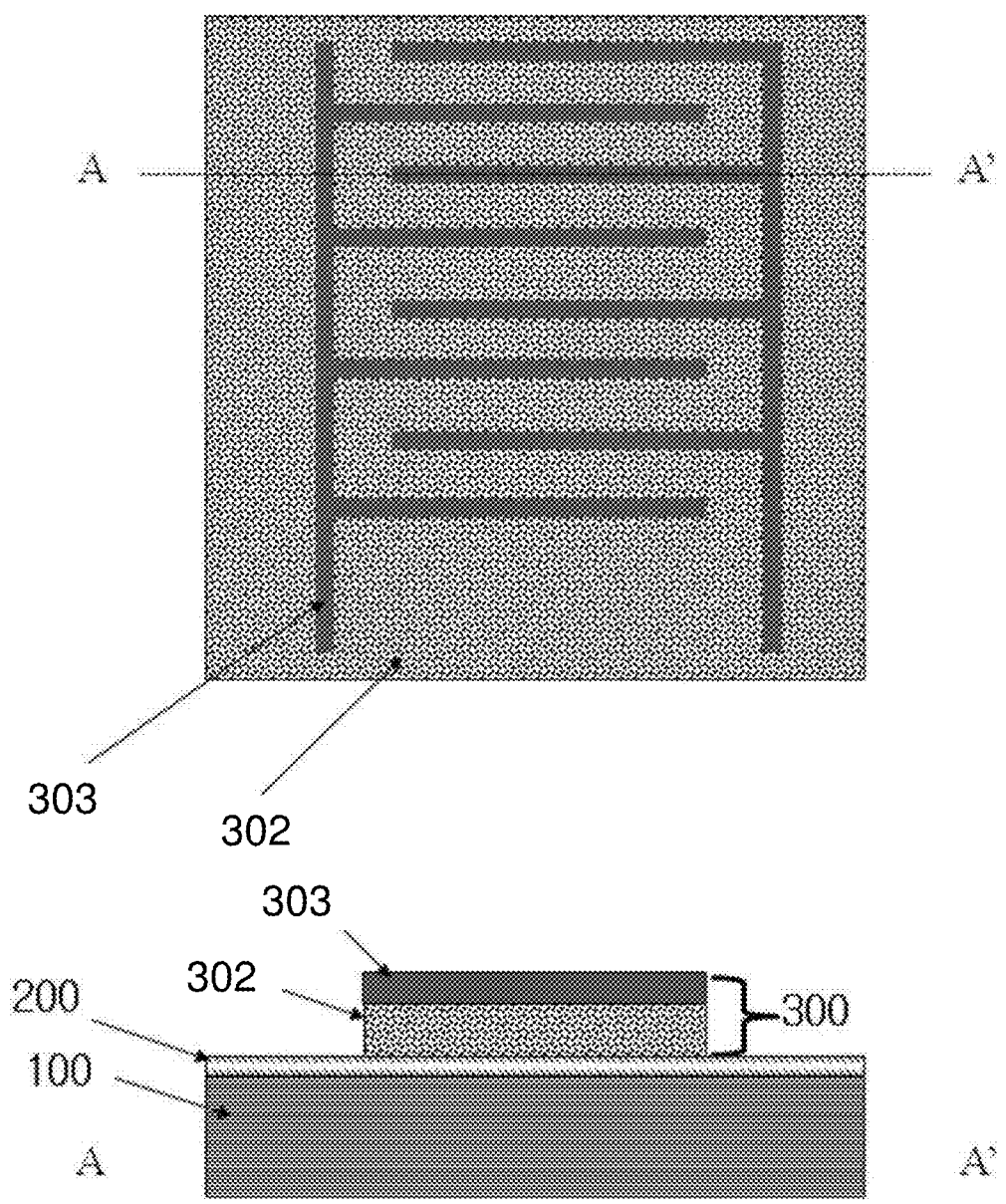

FIG. 4 is a diagram showing a nanogenerator having an IDE structure. In case of a MIM structure, the lower metal electrode is adhered to the buffer layer 200 which is a silicon oxide layer, and in case of an IDE structure, a piezoelectric material layer 302 is adhered to the buffer layer. However, in both cases, the lower electrode or the piezoelectric material layer, which is made of metal, is weakly adhered to a silicon oxide, which is based on silicon. It is estimated that this is caused since the oxide coupled to silicon weakens an adhesive force at a boundary surface of metal and silicon.

Figure 5:
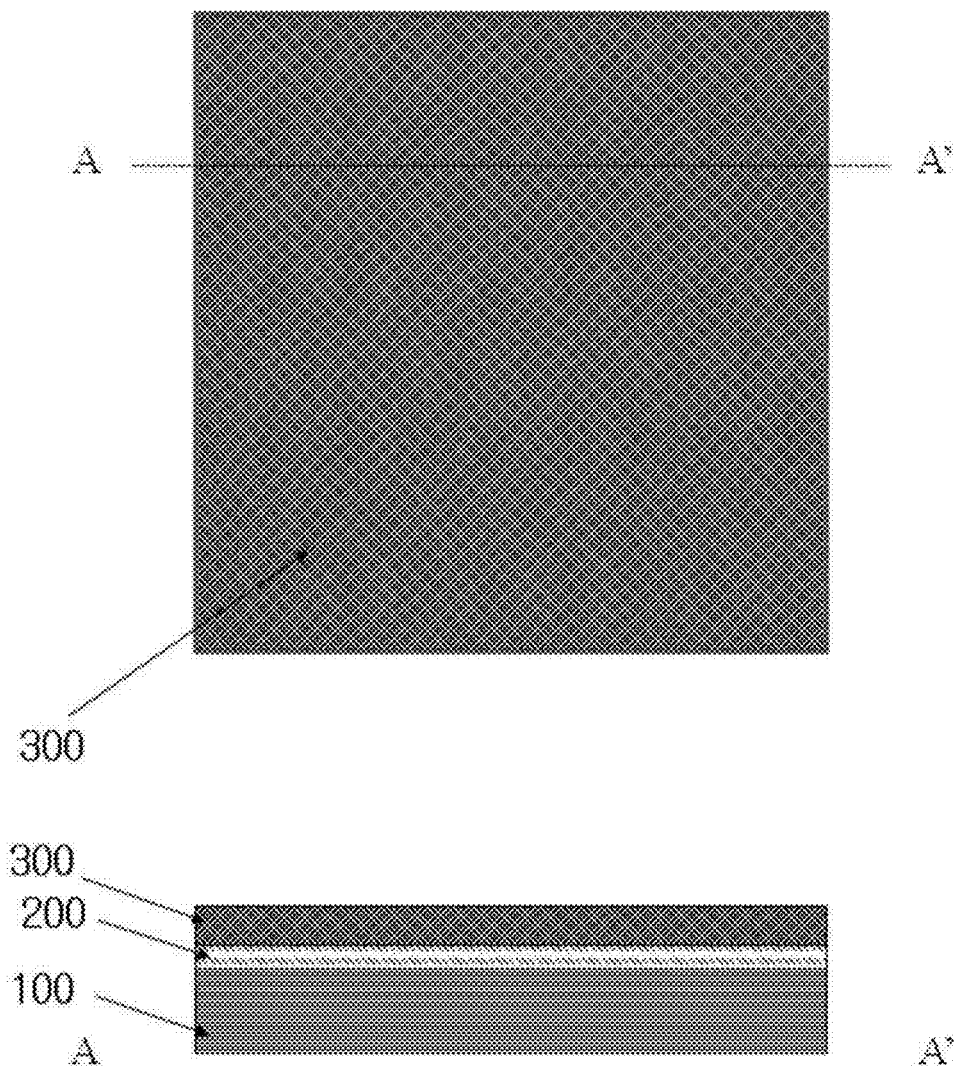

The nanogenerator configured as shown in FIG. 3 or 4 is provided on the buffer layer 200 which is a silicon oxide as shown in FIG. 5, and the nanogenerator 300 is physically connected to the sacrificial substrate 100 at a lower portion by means of the buffer layer 200.

Figure 6:
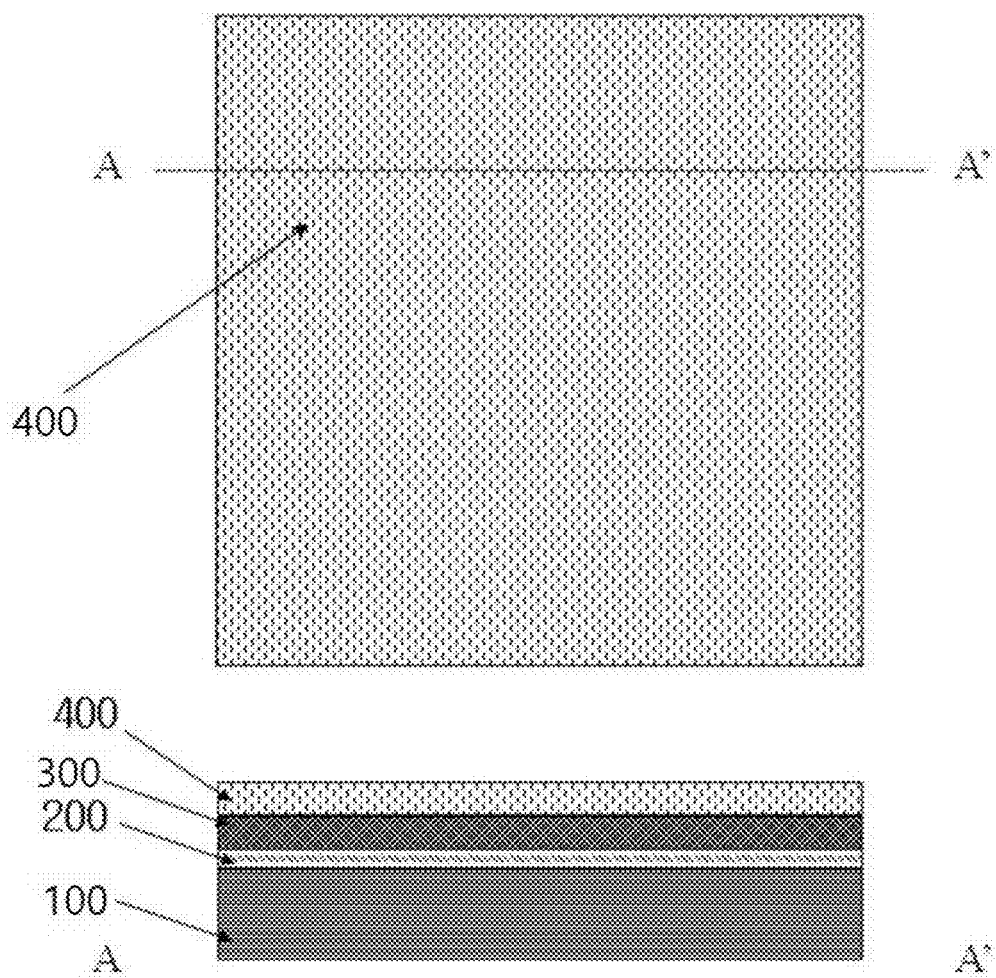

Referring to FIG. 6, the nickel layer 400 serving as a metal layer is laminated on the upper surface of the nanogenerator 300 of FIGS. 3 and 4. According to an embodiment of the present disclosure, the nickel layer 400 may be laminated by means of a common semiconductor process such as sputtering or PVD, and metal coating may also be used for the lamination work. According to the lamination, a nickel 400 adhered onto the nanogenerator 300 is formed.

Figure 7:
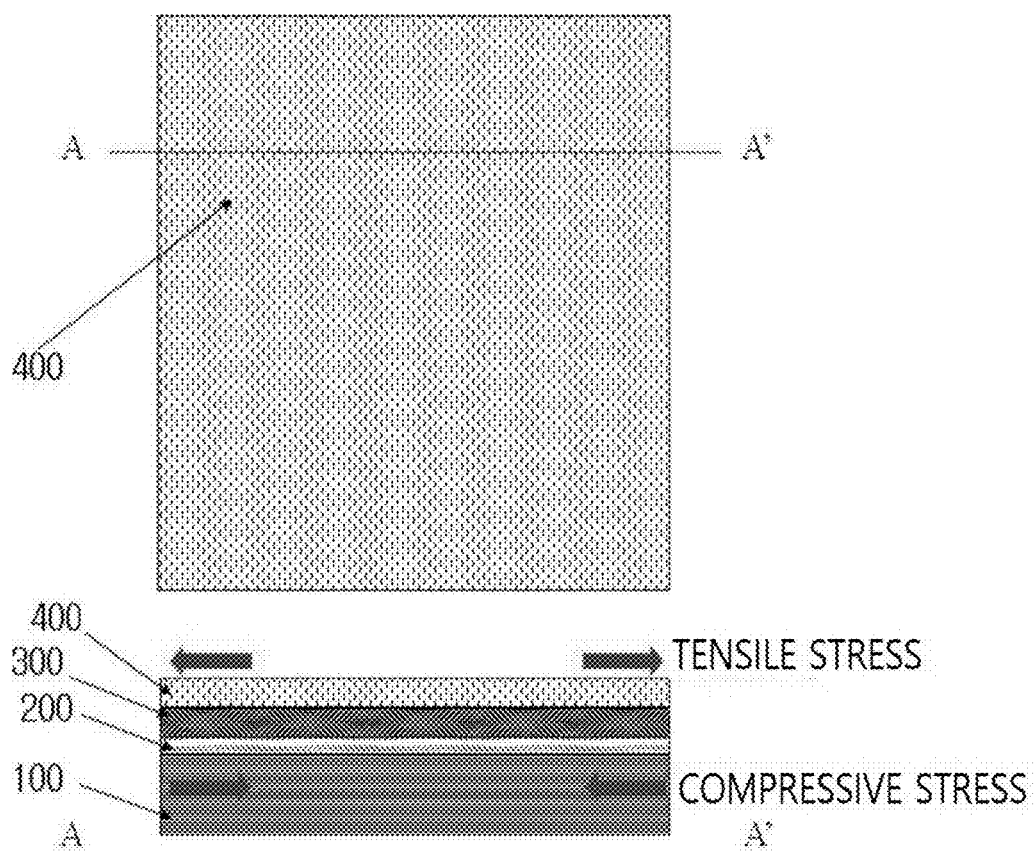

Referring to FIG. 7, a mechanical energy (for example, a physical impact) or a thermal energy is applied to the nickel layer 400 serving as a metal layer having a residual tensile stress. As a result, a residual tensile stress of nickel is generated, which causes a mismatching or asymmetric effect between the residual tensile stress and a residual compressive stress of a silicon substrate indirectly adhered to the nanogenerator by means of the buffer layer. Accordingly, at a boundary surface between the buffer layer 200 and the nanogenerator 300, the adhesion of both layers is released. In the present disclosure, a desired device and substrate is laminated to a metal layer having a tensile stress different from the residual compressive stress of the silicon substrate as described above, and then energy is applied from the outside to separate the device at a weak adhesion surface. In particular, since the separation surface where the device is separated is set as a boundary surface between the nanogenerator and the buffer layer adhered with a weakest force, the device fabricated on the silicon substrate may be intactly separated and transferred. In addition, the separation location of the device may be controlled according to a stress difference between the metal layer and the sacrificial substrate.

Figure 8:
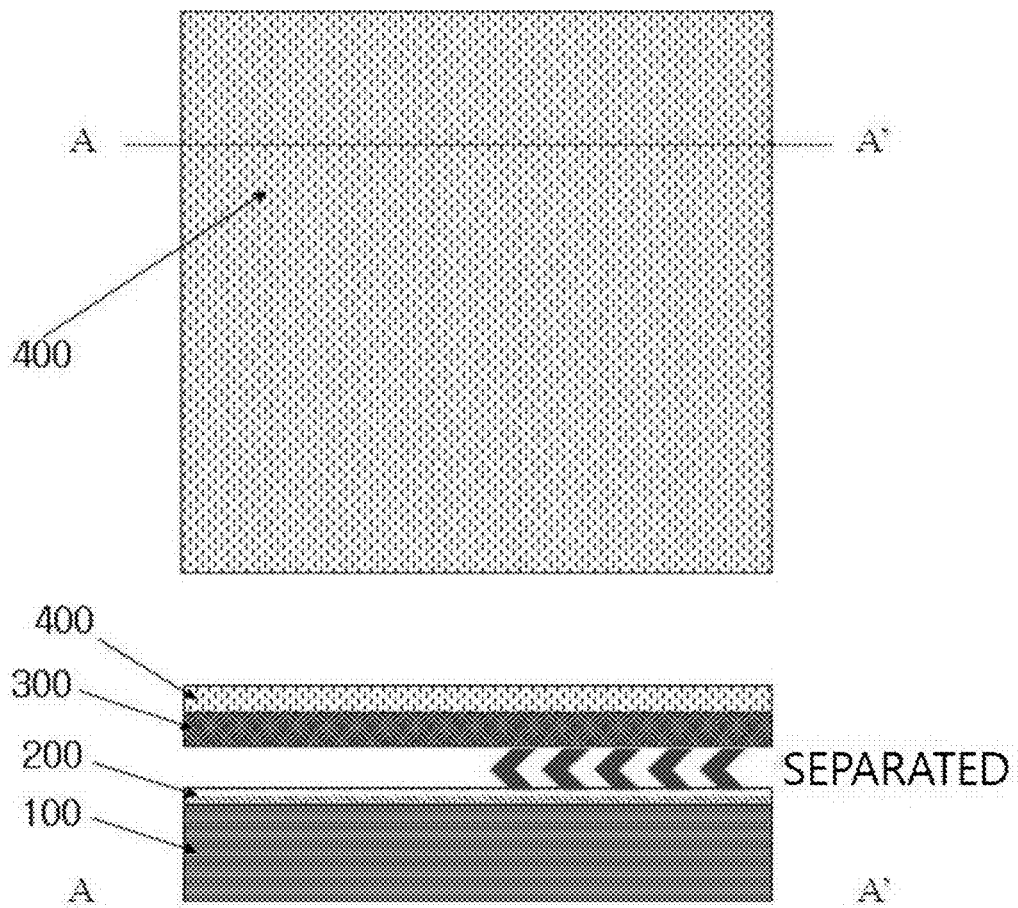
Figure 9:
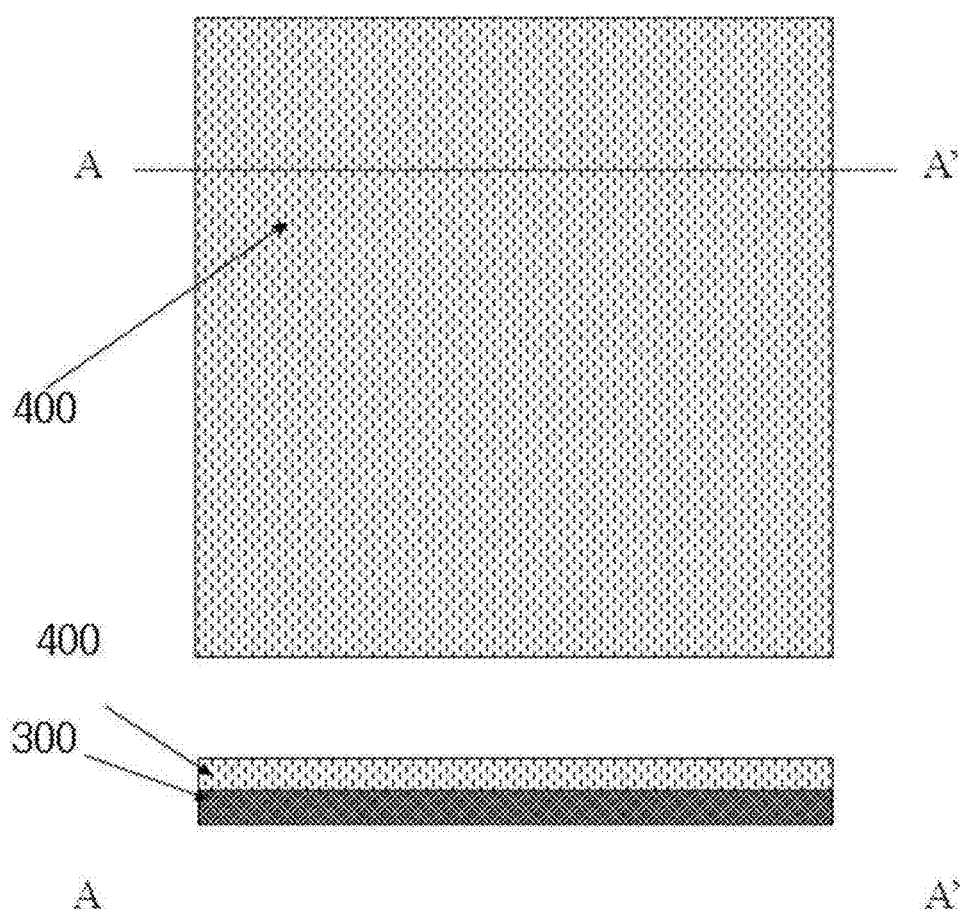

Referring to FIG. 8, the nanogenerator 300 whose adhesion is released due to a mismatching residual tensile stress of the metal layer in contact with the silicon substrate is separated from the silicon oxide buffer layer 200 (see FIG. 9).

Figure 10:
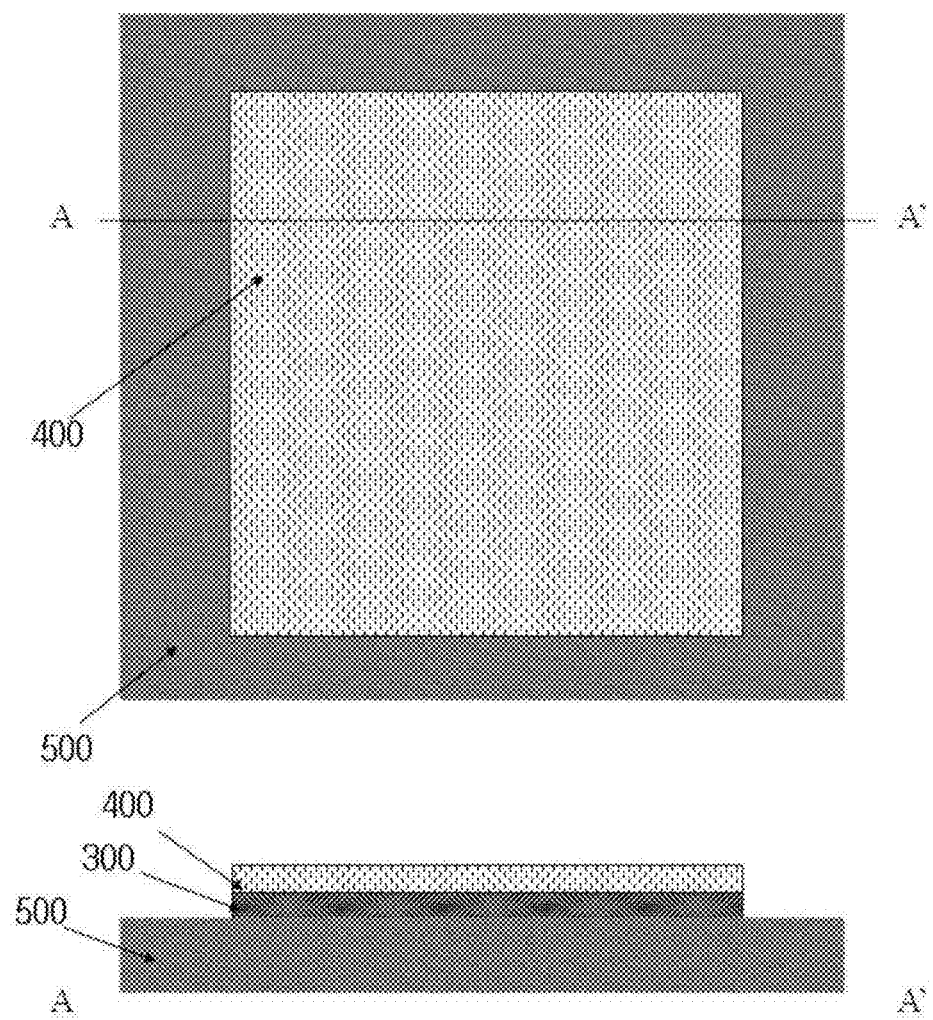

Referring to FIG. 10, the separated nanogenerator 300 and the nickel 400 are moved toward and physically adhered to a flexible substrate 500. By doing so, a flexible nanogenerator transferred to the flexible substrate 500 is completed.

Figure 11:
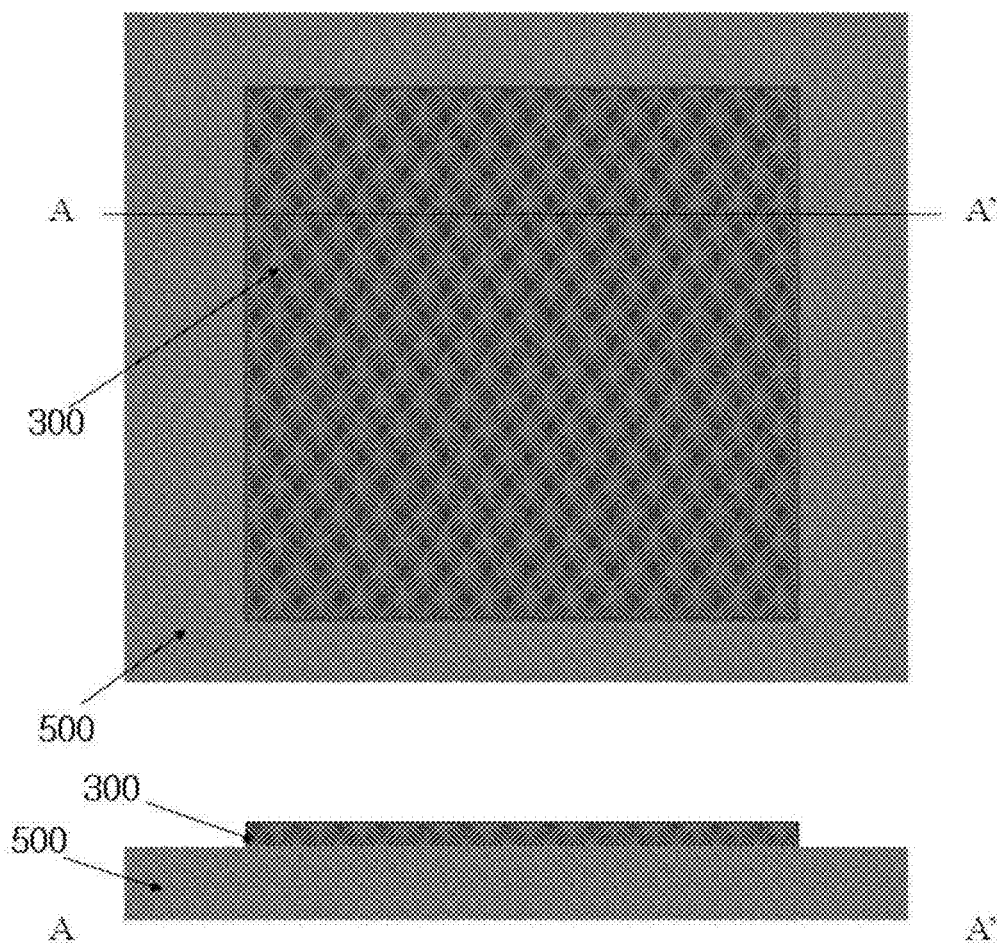

Referring to FIG. 11, the nickel layer 400 is removed by means of a common chemical etching process. For example, the nickel layer 400 may be removed by dipping an upper portion of the device, adhered to the flexible substrate 500, in a specific etching solution used for etching the nickel layer 400. However, the nickel layer 400 may be selectively removed using various metal layer removing methods in addition to above, and they are also included in the scope of the present disclosure.

FIGS. 12 to 15 are diagrams for illustrating a process of forming the nanogenerator 300 and the nickel layer 400 on the sacrificial substrate 100 and then finally transferring the nanogenerator 300 onto the flexible substrate 500 according to an embodiment of the present disclosure, by using actual process photographs and lamination structures.

Figure 12:
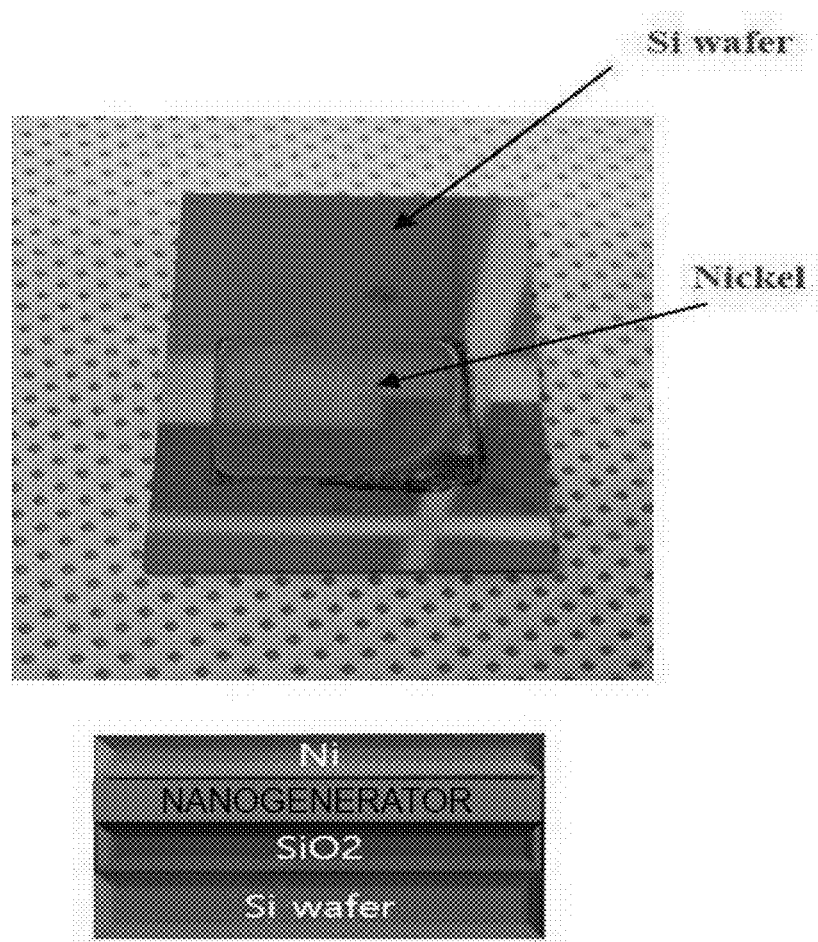
FIGS. 12 to 15 are diagrams for illustrating a process of forming a nanogenerator and nickel layer on the sacrificial substrate.

In FIG. 12, it is depicted that the nickel layer 400 corresponding to a separation induction metal layer is formed on the nanogenerator 300.

Figure 13:
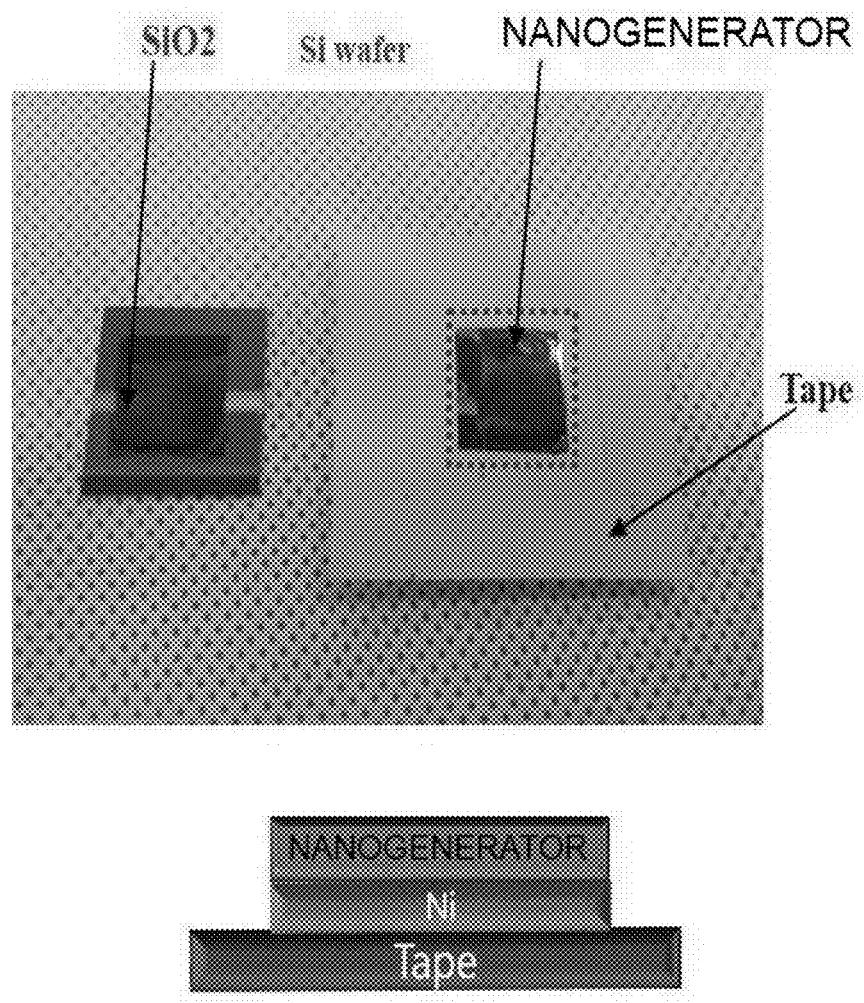

In FIG. 13, it can be found that the nickel layer 400 and the nanogenerator 300 laminated by a transferring release tape attached to the top of the nickel layer 400 is separately disposed on the release tape in a state where a separation is formed between the nanogenerator 300 and the sacrificial substrate 100 due to a stress mismatching due to the residual stress of the nickel layer 400.

Figure 14:
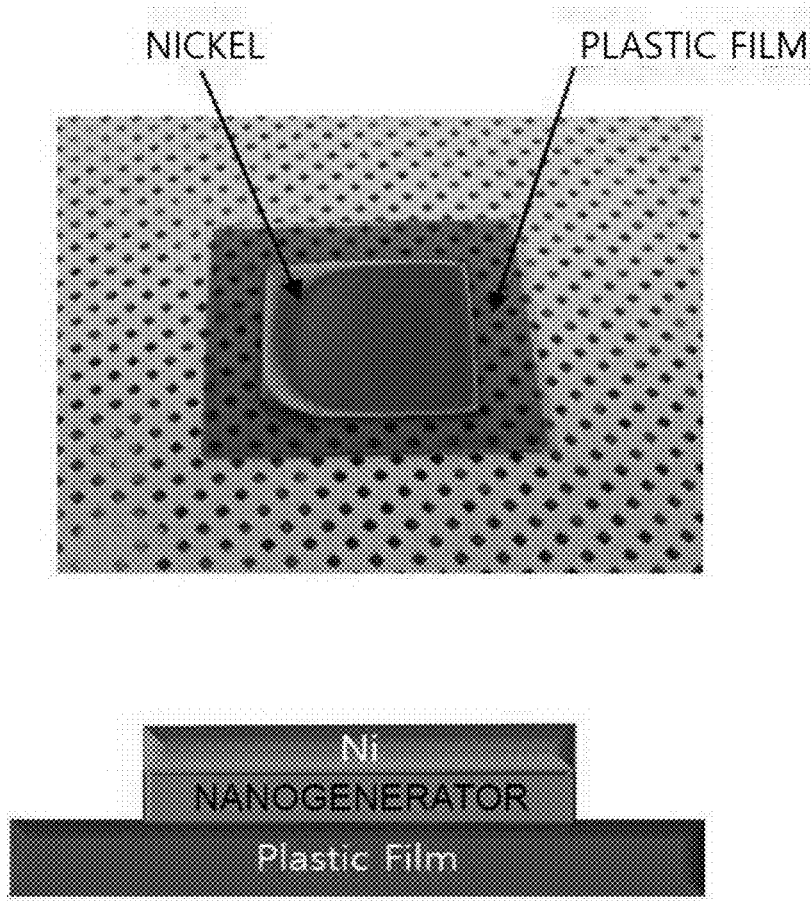

In FIG. 14, it can be found that the nanogenerator 300 and the nickel layer 400 are transferred onto the flexible substrate 500 from the release tape.

Figure 15:
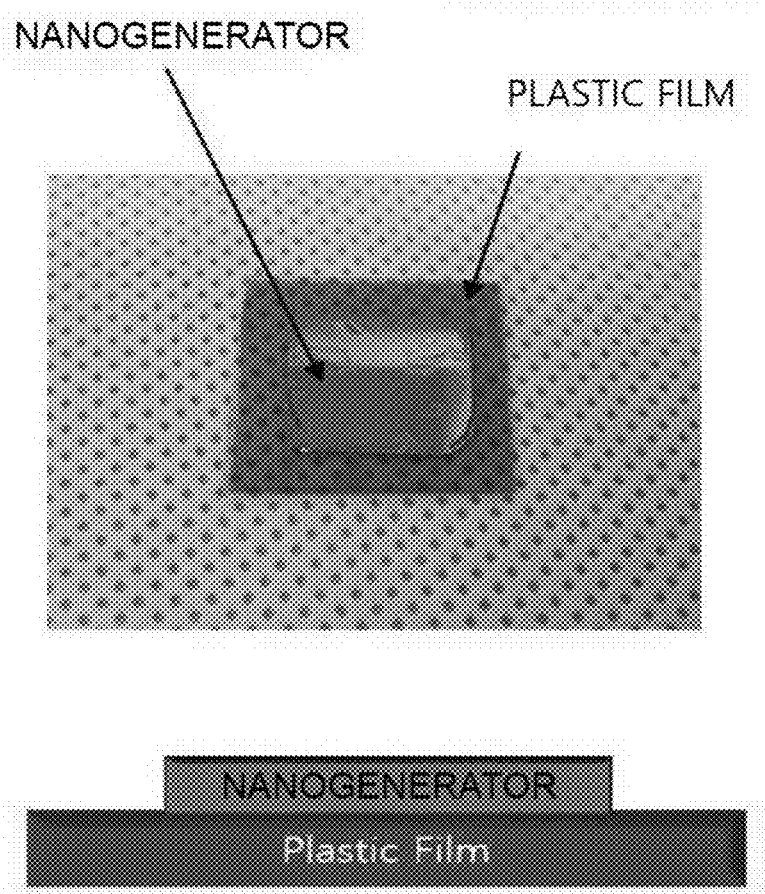

Next, in FIG. 15, it can be found that the nickel layer 400 is etched from the nanogenerator 300 by using an etching ratio between the nickel layer 400 and the nanogenerator 300.

As described above, the present disclosure allows an accurate separation at a boundary surface between the nanogenerator 300 corresponding to a piezoelectric element and the buffer layer 200 serving as a silicon oxide by using a residual tensile stress of the nickel layer 400 serving as a separation induction metal layer, which ensures easy removal of the sacrificial substrate 100 and the buffer layer 200, which are intermediate substances for the generation of a nanogenerator.

As described above, the present disclosure separates a nanogenerator by using a stress difference between the sacrificial substrate and the metal layer, instead of an existing method in which a nanogenerator is separated from the sacrificial substrate by means of wet etching or the like. In particular, according to a difference between a tensile stress at the metal layer such as nickel and a compressive stress at the lower silicon substrate, the nanogenerator is intactly separated from the silicon oxide layer serving as a buffer layer. Therefore, the nanogenerator may be separated from the sacrificial substrate in a mechanical way, which is safer and more economic in comparison to an existing chemical separation method using an etching solution. Further, it is also possible to avoid a damage of the nanogenerator caused by an etching solution.

The flexible nanogenerator manufactured according to the present disclosure receives an electric energy generated from a nanogenerator according to a movement of a living body into which the nanogenerator is inserted, transmits the electric energy to a nerve of the living body to stimulate the nerve, senses and detects movement of a muscle connected to the nerve of the living body, and outputs the detected result as data. In the present disclosure, a nerve in a living body may be artificially stimulated using an electric energy generated at a flexible nanogenerator to allow the muscle to move. The present disclosure provides a bio-stimulus sensing system including the flexible nanogenerator. If the nanogenerator according to the present disclosure is implanted in a living body, an electric energy is generated at the nanogenerator due to the movement of organs or the like in the living body, and an electric stimulus may be applied instead of a damaged nerve, which enhances the curability of a disease. By doing so, the present disclosure may be used as a medical electronic device which provides an electric current of a flexible substrate of a flexible nanogenerator.

It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

While the present invention has been described with respect to the specific embodiments, it will be apparent to those skilled in the art that various changes and modifications may be made without departing from the spirit and scope of the invention as defined in the following claims. Therefore, the embodiments of the present disclosures are not intended to limit the spirit of the present disclosure but to illustrate, and the scope of the present disclosure is not limited by the embodiments. The scope of the present disclosure should be interpreted based on the appended claims, and all technical aspects included in equivalents of the present disclosure should be interpreted as falling within the scope of the present disclosure.

The invention claimed is:

1. A method for separating a nanogenerator, comprising:
   laminating a buffer layer on a sacrificial substrate;
   making a nanogenerator on the buffer layer;
   laminating a metal layer on the nanogenerator; and
   separating the nanogenerator from the buffer layer,
   wherein said separating the nanogenerator from the buffer layer is performed by applying a mechanical or thermal energy to the metal layer, and
   by applying the mechanical or thermal energy to the metal layer, a difference between a residual tensile stress generated at the metal layer and a residual compressive stress at the sacrificial substrate is generated.

2. The method for separating a nanogenerator according to claim 1, wherein the buffer layer is a silicon oxide.

3. The method for separating a nanogenerator according to claim 1, wherein the difference between the residual tensile stress generated at the metal layer and the residual compressive stress at the sacrificial substrate is stronger than an adhesive force between the buffer layer and the nanogenerator.

4. The method for separating a nanogenerator according to claim 1, wherein the sacrificial substrate is a silicon substrate, and the metal layer is a nickel layer.

5. A method for manufacturing a flexible nanogenerator, comprising:
   separating a nanogenerator according to claim 1; and
   transferring the separated nanogenerator to a flexible substrate.

6. A flexible nanogenerator, manufactured by the method defined in the claim 5.

7. A bio-stimulus sensing system, comprising:
   a flexible nanogenerator manufactured by the method defined in the claim 5,
   wherein the bio-stimulus sensing system receives an electric energy generated from the flexible nanogenerator according to a movement of a living body into which the flexible nanogenerator is inserted, and transmits the electric energy to a nerve of the living body to stimulate the nerve.

8. A medical electronic device, comprising a flexible nanogenerator manufactured by the method defined in the claim 5, wherein an electric current generated by bending of the flexible substrate of the flexible nanogenerator is provided to the medical electronic device.

9. A method for manufacturing a flexible nanogenerator, comprising:
   separating a nanogenerator according to claim 2; and
   transferring the separated nanogenerator to a flexible substrate.

10. A method for manufacturing a flexible nanogenerator, comprising:
    separating a nanogenerator according to claim 3; and
    transferring the separated nanogenerator to a flexible substrate.

11. A method for manufacturing a flexible nanogenerator, comprising:
    separating a nanogenerator according to claim 4; and
    transferring the separated nanogenerator to a flexible substrate.

* * * * *